United States Patent [19]

Mechoulam et al.

[11] Patent Number: 5,538,993
[45] Date of Patent: Jul. 23, 1996

[54] CERTAIN TETRAHYDROCANNABINOL-7-OIC ACID DERIVATIVES

[75] Inventors: Raphael Mechoulam; Aviva Breuer; William Devane, all of Jerusalem, Israel; Sumner H. Burstein, Framingham, Mass.

[73] Assignee: Yissum Research Development Company, Jerusalem, Israel

[21] Appl. No.: 192,923

[22] Filed: Feb. 7, 1994

Related U.S. Application Data

[63] Continuation-in-part of Ser. No. 190,089, Feb. 1, 1994.

[30] Foreign Application Priority Data

Sep. 14, 1991 [IL] Israel .......................................... 99418

[51] Int. Cl.[6] ...................... A61K 31/35; C07D 311/80
[52] U.S. Cl. .............................. 514/454; 549/390
[58] Field of Search ............................. 549/390; 514/454

[56] References Cited

U.S. PATENT DOCUMENTS

| | | |
|---|---|---|
| 4,179,517 | 12/1979 | Mechoulam et al. . |
| 4,847,290 | 7/1989 | Burstein . |
| 4,876,276 | 10/1989 | Mechoulam et al. . |
| 5,036,014 | 7/1991 | ElSohly et al. . |
| 5,144,030 | 9/1992 | Wang et al. . |

OTHER PUBLICATIONS

Mechoulam et al., *Tetrahedron: Asymmetry*, vol. 1, No. 5, pp. 315–318 (1990).
Feigenbaum et al., *Proc. Natl. Acad. Sci. USA*, vol. 86, pp. 9584–9587 (1989).
Schwartz et al., *J. Org. Chem.*, vol. 51, pp. 5463–5465 (1986).

*Primary Examiner*—Johann Richter
*Assistant Examiner*—John Peabody
*Attorney, Agent, or Firm*—Pennie & Edmonds

[57] ABSTRACT

The invention relates to compounds of the formula

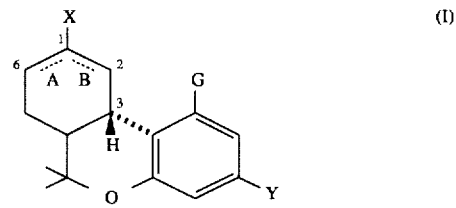

having the (3S,4S) configuration and being essentially free of the (3R,4R) enantiomer, in which A—B indicates an optional 1(2) or 6(1) double bond, X is carboxy, carbalkoxy, or carboxamido, linked to the ring directly or through an alkylene linkage, G is halogen, alkyl, or oxy, and Y is alkyl, oxy, or oxyalkylene. The invention further relates to the synthesis of such compounds, and to pharmaceutical compositions and therapeutic methods in which such compounds may be employed.

24 Claims, 2 Drawing Sheets

CERTAIN TETRAHYDROCANNABINOL-7-OIC ACID DERIVATIVES

CROSS-REFERENCE TO RELATED APPLICATIONS

This is a continuation-in-part of Ser. No. 08/190,089, filed Feb. 1, 1994, which application is in turn a 371 of PCT/US92/07718, filed Sep. 11, 1992.

FIELD OF THE INVENTION

The present invention relates to (3S,4S)-delta-6-tetrahydrocannabinol-7-oic acids and homologs and derivatives thereof, and to processes for their preparation. The invention also relates to pharmaceutical compositions that contain said compounds as active ingredients and that have a wide variety of therapeutic activities, including anti-inflammatory, analgetic, leucocyte anti-adhesion, anti-platelet activating factor (PAF), and anti-glaucoma activities. Such compositions also have the ability to alleviate certain symptoms due to neuronal injury or loss.

BACKGROUND OF THE INVENTION

The (3S,4S) enantiomers of cannabimimetically active cannabinoids, such as the natural (3R,4R)-delta-1-tetrahydrocannabinol (THC), are generally not cannabimimetic. This lack of undesirable CNS side effects makes them suitable as therapeutic agents. It has been previously shown that the (3S,4S)-7hydroxy-delta-6-tetrahydrocannabinol 1,1-di-methylheptyl homolog (compound 1a in FIG. 1) is an analgetic, entiemetic, and anti-NMDA drug [U.S. Pat. No. 4,876,276; Mechoulam, R., et al., Tetrahedron:Asymmetry, 1, 315(1990); Feigenbaum, J. J., et al., Proc. Natl. Acad. Sci., 86, 9584 (1989)]. It has also been shown that (3R,4R)-delta-1-tetrahydrocannabinol-7-oic acid (FIG. 1 compound 2), which also shows no psychotropic effects, is an antiinflammatory and analgetic compound [U.S. Pat. No. 4,847,290]. However, the (3S,4S)-tetrahydrocannabinol-7-oic acids have not yet been prepared and their therapeutic activity has been unknown so far. These compounds have now been synthesized and were found to possess unexpected therapeutically important properties.

SUMMARY OF THE INVENTION

The present invention provides (3S,4S)-delta-6-tetrahydrocannabinol-7-oic acids and homologs and derivatives thereof having the general formula:

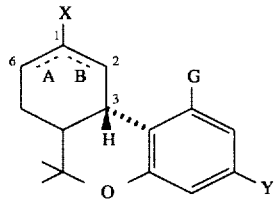

(GF)

wherein the variable substituents are as described hereinbelow. The present invention also provides methods of treatment of injuries to the central nervous system associated with excitatory amino acid neurotoxicity which comprise administering to patients therapeutically effective amounts of pharmaceutical compositions that contain as an active ingredient an effective quantity of a compound of the invention. A further aspect of the present invention is a method for blocking N-methyl-D-aspartate (NMDA) receptors in a patient which comprises administering to said patient a therapeutically effective amount of a pharmaceutical composition containing as active ingredient an effective quantity of a compound of the invention. Compounds according to the present invention are characterized by various beneficial properties such as analgesic, anti-emetic, sedative, anti-inflammatory, anti-glaucoma, and neuroprotective activities.

DESCRIPTION OF THE PREFERRED EMBODIMENTS

The compounds of the present invention have the general structural formula:

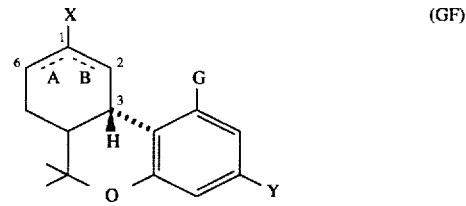

(GF)

In accordance with the present invention, said compounds have the (3S,4S) configuration and are essentially free of the (3R,4R) enantiomer. The variable A—B indicates an optional 1(2) or 6(1) double bond, X is —C(O)OR" wherein R" is hydrogen or $C_1$–$C_5$ alkyl optionally containing a terminal —OR''' or —OC(O)R''' moiety wherein R''' is hydrogen or $C_1$–$C_5$ alkyl, —R'C(O)OR" wherein R' is $C_1$–$C_5$ alkyl and R" is hydrogen or $C_1$–$C_5$ alkyl optionally containing a terminal —OR''' or —OC(O)R''' moiety wherein R''' is hydrogen or $C_1$–$C_5$ alkyl, —C(O)N(R")$_2$ wherein each R", which may be the same or different, is hydrogen or $C_1$–$C_5$ alkyl optionally containing a terminal —OR''' or —OC(O)R''' moiety wherein R''' is hydrogen or $C_1$–$C_5$ alkyl, or —R'C(O)N(R")$_2$ wherein R' is $C_1$–$C_5$ alkyl and each R", which may be the same or different, is hydrogen or $C_1$–$C_5$ alkyl optionally containing a terminal —OR''' or —OC(O)R''' moiety wherein R''' is hydrogen or $C_1$–$C_5$ alkyl, G is —X wherein X is halogen, —R' wherein R' is $C_1$–$C_5$ alkyl, —OR" wherein R" is hydrogen or $C_1$–$C_5$ alkyl optionally containing a terminal —OR''' or —OC(O)R''' moiety wherein R''' is hydrogen or $C_1$–$C_5$ alkyl, or —OC(O)R" wherein R" is hydrogen or $C_1$–$C_5$ alkyl optionally containing a terminal —OR''' or —OC(O)R''' moiety wherein R''' is hydrogen or $C_1$–$C_5$ alkyl, and Y is $C_1$–$C_{12}$ straight chain or branched alkyl, —OR'''' wherein R'''' is a straight-chained or branched $C_2$–$C_9$ alkyl which may be substituted at the terminal carbon atom by a phenyl group, or —(CH$_2$)$_n$OR''' wherein n is an integer of from 1 to 7 and R''' is hydrogen or $C_1$–$C_5$ alkyl.

It is stressed that all the compounds are of the (+)-(3S,4S) configuration, essentially free of the (–)-(3R,4R) enantiomer. The compounds of the type defined by general formula (GF) are substantially devoid of "cannabis-type" CNS activity.

Preferred specific compounds according to the above formula are those: wherein A—B indicates a 6(1) double bond, X is carboxy, G is acetoxy, and R is 1,1-dimethyl heptyl; wherein A—B indicates a 6(1) double bond, X is N,N-diethylcarboxamide, G is acetoxy, and R is 1,1-dimethyl heptyl; and wherein A—B indicates a 6(1) double bond, X is N-β-hydroxyethylcarboxamide, G is acetoxy, and R is 1,1-dimethyl heptyl.

Figure 1A:
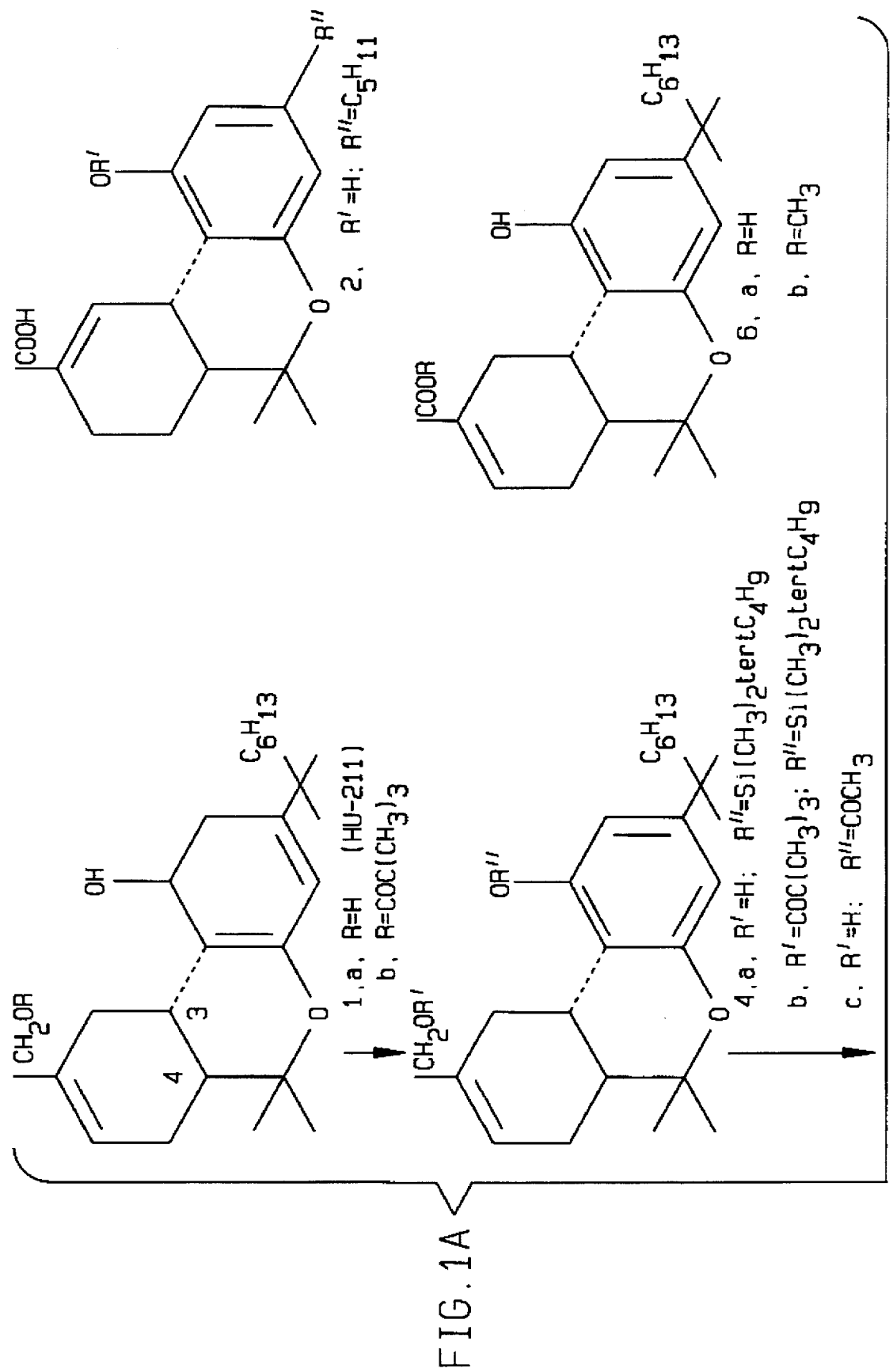
FIG. 1 provides structural formulae for several compounds according to the present invention as well as relevant prior art compounds, and illustrates a synthetic process according to the present invention by means of a structural flowchart.
Figure 1B:
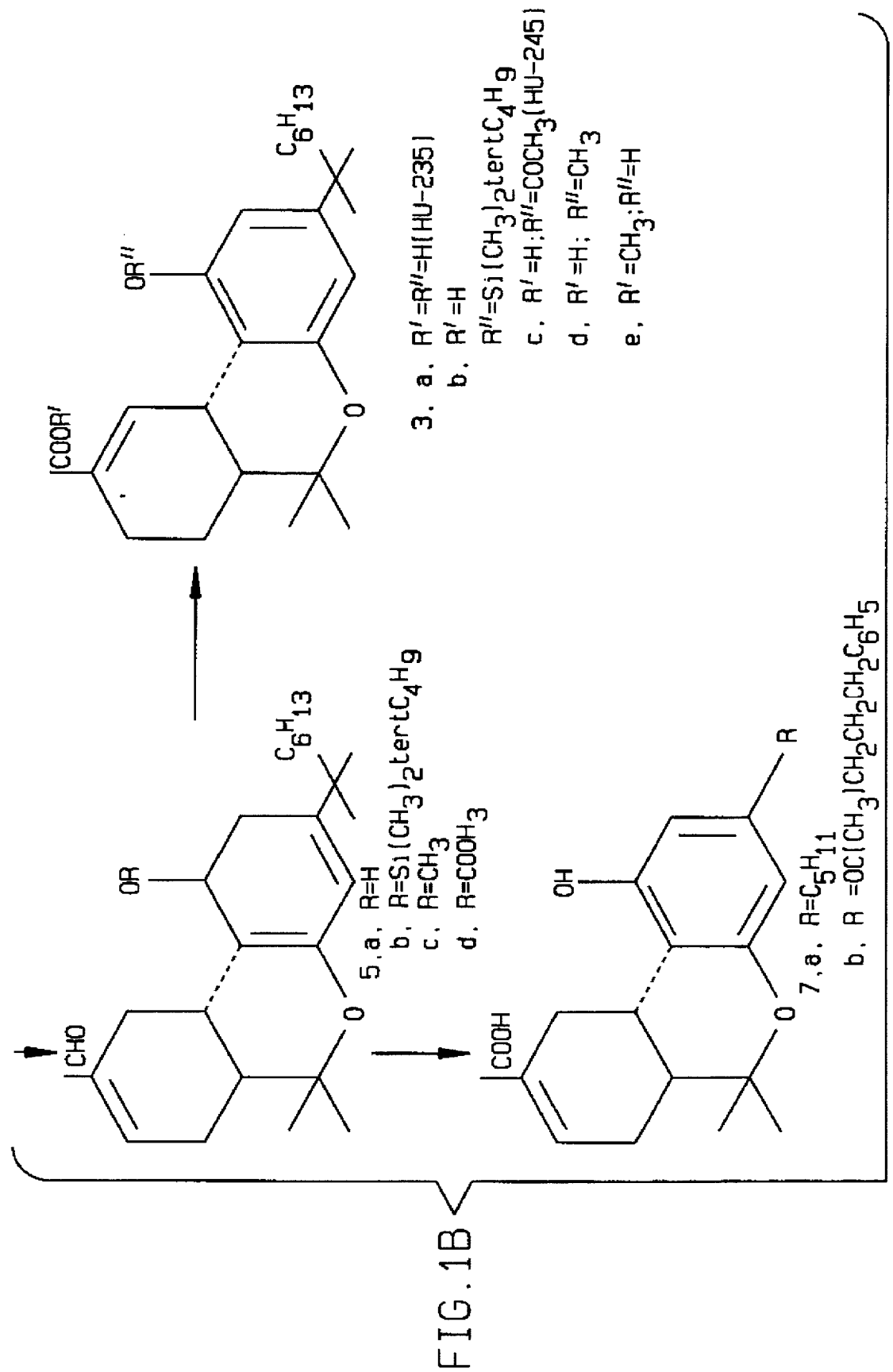

The most preferred compounds are the 1,1-dimethylheptyl homologs of (3S,4S)-(+)-delta-6-tetrahydrocannabinol-7-oic acid (hereafter designated HU-235, compound 3a in FIG. 1) and its acetate (hereafter designated HU-245, compound 3c in FIG. 1). Dimethylheptyl embodiments of Y are found in THC and its analogues. However, for the neuroprotective activity which characterizes the present invention, it is believed that any lower or mid-range alkyl substituent will be suitable at the Y position.

A preferred subgroup of compounds according to the present invention are represented by the formula:

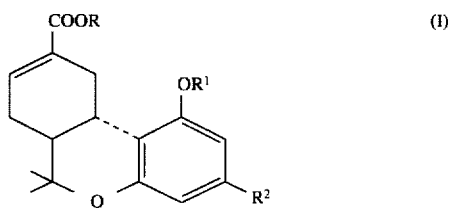
(I)

herein R is a hydrogen atom or a $C_1$–$C_5$ alkyl group, $R^1$ is a hydrogen atom or a $C_1$–$C_5$ acyl group, and $R^2$ is selected from the group consisting of: (a) a straight-chained or branched $C_1$–$C_{12}$ alkyl; (b) a group —O—$R_4$, wherein $R_4$ is a straight-chained or branched $C_2C_9$ alkyl which may be substituted at the terminal carbon atom by a phenyl group; and (c) a group —$(CH_2)_n$-O-alkyl, where n is an integer of from 1 to 7 and the alkyl group contains from 1 to 5 carbon atoms.

Particularly preferred are compounds according to that formula wherein R is hydrogen, $R^1$ is hydrogen or methyl, and $R^2$ is 1,1-dimethylheptyl

Synthetic Methods

The invention also relates to processes for the preparation of compounds of general formula (GF).

In a first embodiment the process for the preparation of a compound of formula (GF) wherein X is carboxy or carbalkoxy comprises:

(a) reacting a compound of the formula:

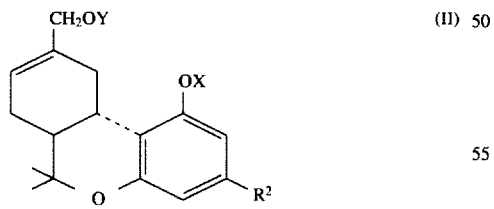
(II)

wherein Y is a straight-chained or branched $C_1$–$C_5$. alkyl, for example, (trimethyl)methyl, X is a suitable protective group, for example, dimethyl-tert.butylsilyl or phenylsilyl, a $C_1$–$C_5$ alkyl group, or benzyl, and $R^2$ is $C_1$–$C_{12}$ straight chain or branched alkyl, —OR"" wherein R"" is a straight-chained or branched $C_2$–$C_9$ alkyl which may be substituted at the terminal carbon atom by a phenyl group, or —$(CH_2)_n$OR'" wherein n is an integer of from 1 to 7 and R'" is hydrogen or $C_1$–$C_5$ alkyl, with a suitable reducing agent to give the corresponding allylic alcohol of formula III:

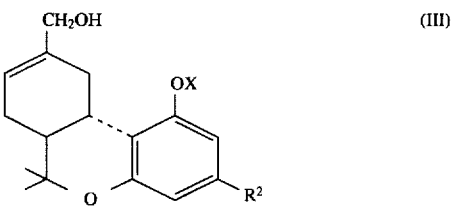
(III)

(b) oxidizing the alcohol of formula III with a suitable oxidizing agent to give the corresponding aldehyde of formula IV:

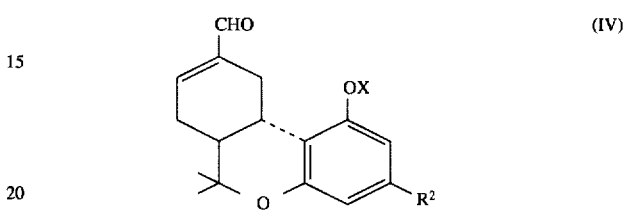
(IV)

(c) oxidizing the aldehyde of formula IV with a suitable oxidizing agent to give the corresponding allylic acid of formula V:

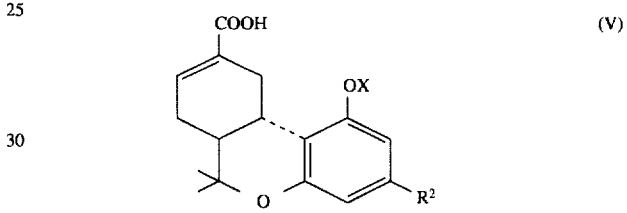
(V)

and (d) removing the protective group X by standard procedures to give the acid according to formula (I).

In stage (a), the protective group OY may optionally be replaced by the group —$NR^4R^5$, wherein $R^4$ and $R^5$ are $C^1$–$C^5$ alkyl groups.

The reducing agent can be, for example, lithium aluminum hydride.

In a second embodiment compounds of general formula (GF) wherein the substituents are as defined above may be prepared as follows:

(a) subjecting a compound of the formula:

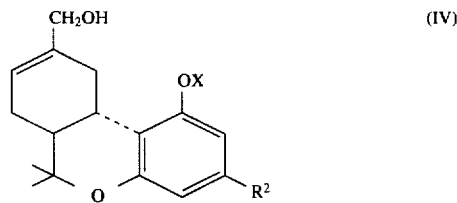
(IV)

wherein $R^2$ is as defined above to selective esterification, to give the corresponding phenolic ester of formula VII:

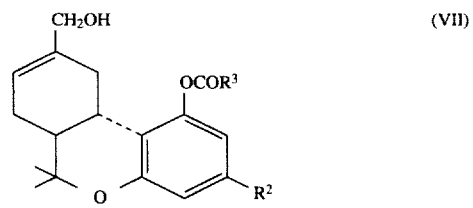
(VII)

wherein $R^3$ is a $C_1$–$C_5$ alkyl, or benzyl which may be substituted at the para position by chlorine or bromine;

(b) oxidizing the ester of formula VII with a suitable oxidizing agent to give the corresponding aldehyde of formula VIII:

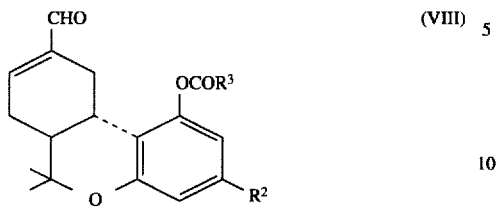

(c) oxidizing the aldehyde of formula VIII with a suitable oxidizing agent to give the corresponding acid of formula I:

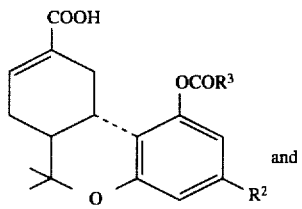

and optionally removing the ester group $COR^3$ to give the corresponding compound:

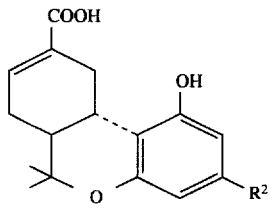

According to a first embodiment, the pathway of which is illustrated in FIG. 1, the starting material is 7-hydroxy-delta-6-tetrahydrocannabinoldimethylheptyl (1a)(HU-211) (which may be prepared according to the procedure reported by Mechoulam, R., et al., Tetrahdron: Asymmetry, 1, 315 (1990)), protected at the 7-position by conventional protective groups, for example pivalate (compound 1.b), the phenolic group also being protected by a conventional protective group, for example dimethyltert.butylsilyl (compound 4b). This protected starting material is reduced, for example, by lithium aluminum hydride, to give the corresponding allylic alcohol (compound 4a). The alcohol is then oxidized, for example with chromic oxide in pyridine, to give the corresponding aldehyde (compound 5b). Other oxidizing agents, for example, tert.-butyl chromate, chromic acid/pyridine complex or related chromate derivatives or manganese dioxide, particularly in the presence of cyanide, or related manganese derivatives may be used. The aldehyde is further oxidized, for example with sodium chlorite, to give the corresponding allylic acid (compound 3b). Other oxidizing agents such as manganese dioxide in the presence of sodium cyanide and acetic acid and related manganese derivatives may be used. The phenolic protective group is then removed, to give the desired acid (compound 3a, HU-235). This synthetic route may yield a series of related compounds, which were prepared.

The second embodiment also uses 7-hydroxy-delta-6-tetra-hydrocannabinol-DMH (Compound 1a) as the starting material. This starting material is subjected to selective esterification to give the monoacetate (compound 4c), which on oxidation with, for example, chromic acid in pyridine gives the aldehyde (compound 5d), which is further oxidized to the acid (compound 3c, HU-245). Other oxidizing agents, as above, may be used. Removal of the phenolic protective group leads to the desired acid (compound 3a, HU-235).

Therapeutic Methods

The invention also relates to pharmaceutical compositions which possess potent analgetic, anti-inflammatory, anti-emetic, anti-glaucoma, anti-platelet activating factor and leukocyte anti-adhesion activities, containing compounds of general formula (GF) as active ingredient. These compositions also reduce and may even prevent excitatory amino acid neurotoxicity due to acute injury to the central nervous system, such as injuries due to prolonged epileptic seizures, compromised or reduced blood supply, deprivation of glucose supply and mechanical trauma. The compositions are of special value in grand mal seizure, global-hypoxic ischemic insults, in hypoxia, alone or in combination with blood flow reduction (ischemia), as well as in cases of abrupt occlusion of cerebral arteries (stroke). The compositions of the present invention may also be effective in alleviating certain chronic degenerative diseases associated with gradual selective neuronal loss, mainly Huntington's chorea, Parkinsonism and Alzheimer's disease. The compositions of the present invention have also been discovered to be effective in the treatment of multiple sclerosis. The compositions of the present invention are also useful in the treatment of poisoning affecting the central nervous system, for example strychnine, picrotoxin or organophosphorous poisoning.

The novel compositions contain in addition to the active ingredient conventional pharmaceutically acceptable carriers, diluents and the like. Solid compositions for oral administration such as tablets, pills, capsules or the like may be prepared by mixing the active ingredient with conventional, pharmaceutically acceptable ingredients such as corn starch, lactose, sucrose, sorbitol, talc, stearic acid, magnesium stearate, dicalcium phosphate and gums with pharmaceutically acceptable diluents. The tablets or pills can be coated or otherwise combined with pharmaceutically acceptable materials known to provide a dosage form affording prolonged action or sustained release. Other solid compositions can be prepared as suppositories for rectal administration. Liquid forms may be prepared for administration or for injection, the term including sub-cutaneous, transdermal, intravenous, intrahecal, etc. administration. The liquid compositions include aqueous solutions, flavored syrups, aqueous or oil suspensions, flavored emulsions with edible oils, as well as elixirs and similar pharmaceutical vehicles. In addition, the compositions of the present invention may be formed as aerosol, for intranasal and like administration.

The active dose for humans is generally in the range of from 0.005 mg to about 50 mg per kg body weight, in regimen of 1–4 times a day. However, administration every two days may also be possible, as the drug has a rather prolonged action. The preferred range of dosage is from 1.0 mg to about 20 mg per kg body weight. However, it is. evident to those skilled in the art that dosages would be determined by the attending physician, according to the disease to be treated, method of administration, patient's age, weight, counterindications and the like.

All the compounds defined above are effective in treating the above conditions and can be used as active ingredients of pharmaceutical compositions for treatment of one, or simultaneously several, of the symptoms or disorders defined above. The effective dosages are essentially similar.

The invention also relates to use of the compositions of the present invention for the treatment of the various pathological conditions described above. Administration of therapeutically effective amounts of the compositions of the present invention as used herein encompasses oral, parenteral, intravenous, intramuscular, sub-cutaneous, transdermal, intratechal, rectal and intra-nasal administration.

PREPARATORY EXAMPLES

1. Synthesis of the dimethyl-tert-butylsilyl ether (4a)

The ester (1b) (2.9 g, 6.17 mmoles), $[\alpha]D+152.6°$ (c, 17.2 mg/ml, $CHCl_3$), was dissolved in dry dimethylformamide (DMF) (6 ml.). Dimethyl-tertbutylsilyl chloride (1.85 g, 12.27 remoles) and imidazole (1.67 g, 24.6 remoles) were added and the restilting mixture was stirred for 48 hours at 38° C. Water (30 ml) was added and the mixture was extracted with ether. After evaporation of the dried ether layer an oil (4b) (3.6 g) was obtained; $[\alpha]D+153°$ (c, 24.45 mg/ml, $CHCl_3$); I.R. max (neat) 1725 $cm^{-1}$. No free hydroxyl groups were observed; $^1H$ NMR δ ($CDCl_3$) 3.28 (1H, br d, J=16 Hz, C-2 equat. H), 4.46 (2H, s, C-7H), 5.70 (I H, m, C-6H), 6.38 (1H, d, J-1.5 Hz, arom.), 6.42 (1- H, d, J=1.5 Hz, arom). This oil (compound 4b) was used in the next step) with no further purification.

A solution of compound (4b) (3.2 g, 5.5 mmoles) in dry ether (50 ml) was added under a nitrogen atmosphere to lithium aluminum hydride (870 mg) in dry ether (60 ml). The resulting mixture was boiled under reflux for 1.5 hours. After the usual work up (ethyl acetate followed by slow addition of a saturated solution of magnesium sulphate until a clear ether supernatant is formed) the ether layer was dried and evaporated to give an oil (3.2 g). The oil was chromatographed on a silica gel column (100 g), using ether:petroleum ether (6:4) as eluent, to give the alcohol (4a) (8 g, 67%); $[\alpha]D+175°$; (7.6 mg/ml, $CHCl_3$) I.R. max (neat) 3320 $cm^{-1}$ (OH band); no carbonyl bands; $^1H$ NMR δ ($CDCl_3$) δ 3.38 (1H, br d, J=16 Hz, C-2 equat. H) 4.02 (2H, s, C-7H), 5.72 (I H, br d, C-6H), 6.36, 6.42 (2H, s, aromatic).

2. Synthesis of aldehyde (5b)

Dry pyridine (2.3 ml), followed by chromic oxide (1.44 g, 14.4 remoles) were added to a solution of methylenechloride: DMF (4:1) (36 ml). The mixture was stirred for 15 min. The primary allylic hydroxy compound (4a) (1.8 g, 3.6 mmoles) in methylchloride: DMF (4:1) (7.2 ml) was added and the reaction mixture was stirred at room temp. for 1 hr. Ethanol (1.8 ml) was added, the mixture was stirred for additional 10 min., and was then diluted with ethylacetate (180 ml). The resulitng mixture was filtered through a sintered glass funnel, packed with silica (3 cm), with a layer of anhydrous sodium sulfate on top, and eluted with ethyl acetate (ca 600 ml). The ethyl acetate filtrate was washed with dilute hydrochloric acid (1N), then with sodium bicarbonate solution and water. After evaporation of the dried organic solvent a semisolid compound (5b) (1.7 g, 95%) was obtained. Crystallization from pentane gave the aldehyde (5b); m.p. 80°–81° C.; $[\alpha]^D+268°$ (C, 6.82 mg/ml, $CHCl_3$); I.R. max 1690$cm^{-1}$ (neat); $^1H$ NMR δ ($CDCl_3$) 3.82 (1H, br d, J=15 Hz, C-2 equat. H), 6.38 and 6.42 (2H, s, aromatic), 6.80 (I H, m, C-6H), 9.50 (1H, s, c-7H). Anal. ($C_{31}H_{50}O_3Si$) C H.

3. Synthesis of (3R, 4R) -delta-6-THC-DMH-7-oic acid (3a)

Sodium chlorite (488 mg) was added portionwise with vigorous stirring to a mixture of the aldehyde (5b) (498 mg, 1 mmole), 2-methyl-2-butene (2.24 ml), saturated aqueous potassium dihydrogenphosphate (1.34 ml) and t-butanol (22 ml). The reaction mixture was stirred at room temp. for 5 hrs. Water (20 ml) was added and the mixture was extracted several times with ethyl acetate, dried and evaporated to give the crude acid which was purified on a silica gel column (10 g, elution with 10% ether:pet.ether) to give the acid (3b) (460 mg, 89%) as an oil; $[\alpha]^D+218°$ (c, 13.7 mg/ml, $CHCl_3$); I.R. max 1680, $CM^{-1}$; and a broad band in the 2800–3600 region; $^1H$ NMR δ 3.75 (1H, br d, J=18 Hz, C-2 equat. H), 6.23 (1H, d, J=1.5, arom.), 6.27 (I H, d, J=1.5, arom.), 7.00 (1H, m, C-6H).

Tetrabutylammonium fluoride (0.6 mmoles solution in THF) was added by injection under a nitrogen atmosphere to a cold solution (ice bath) of the acid (3b) (280 mg, 0.54 mmoles) in tetrahydrofuran (THF) (3 ml). The resulting solution was stirred at 0° for 15 minutes. Water was added and the mixture extracted several times with ether. The ether layer was dried and evaporated to give the crude product. The product was further purified on a silica gel column with ether:petroleum ether (1:1) as eluent. The solid thus obtained (140 ng, 56%) was crystallized from acetonitrile to give the acid (3a) m.p. 112–11.4 (sintering); $[\alpha]^D+275°$ (c, 3.8 mg/ml, $CHCl_3$), I.R. max (Nujol) 1680 $cm^{-1}$ and a broad band in the 3100–3600 region; $^1H$ NMR δ 3.82 (1H, br d, J=18 Hz, C-2 equat.H), 6.22 (1H, d, J=1.5 Hz, atom.) 6.38 (1H, d, J=1.5 arom). 7.16 (1H, m, C-6H); M/z 400 (M). The acetate (3c), (HU-245), melts at 120°–122°; $[\alpha]^D+265°$ (c, 9.0 mg/ml, $CHCl_3$) T.R. max (Nujol) 1760 $cm^{-1}$ and a broad band in the 3100–3600 $cm^{-1}$ region; $^1H$ NMR ($CDCl_3$) δ 2.30 (3H, s, $OCOCH_3$), 3.38 (1H, br d, J=19 Hz, C-2 equat. H), 6.56, (1H, d, J=1.5 Hz arom.) 6.68 (1 fl, d, j=1.5 atom.), 7.18 (1H, m, C-6H). Anal. ($C_{27}H_{38}O_5$) C, H. The methyl ether (3d) melts at 172°–174°; $[\alpha]^D$ +270° (7.5 mg/ml, $CHCl_3$); I.R. max (KBr) 1660, 1680 $cm^{-1}$ and a broad band in the 3100–3600 region; ($CHCl_3$) 1696 $cm^{-1}$; $^1H$ NMR ($CDCl_3$) 3.76 (1H, br d, J=18 Hz, C-2 equat. H), 3.80 (3H, s, $OCH_3$), 6.39, 6.42, (2H, s, aromatic), 7.16 (I H, m, C-611); MS m/z 414 ($M^+$). Anal. ($C_{26}H_{38}O_4$) C, H.

4. Synthesis of aldehyde (5a)

Tetrabutylammonium fluoride (0.4 mmoles, soln. in THF) was added, by injecton to a cold solution (ice bath) of the aldehyde (5b) (200 mg, 0.4 mmoles-) in THF (4 ml), under a nitrogen atmosphere. The solution was stirred at 0° C. for 5 minutes and then at room temperature for 15 minutes. The solvent was evaporated and the residue was separated on a silica gel column (10 g). The product was eluted with ether:petroleum ether (15:85). The solid obtained (120 mg, 78%) was crystallized from pentane to give the required compound (5a) m.p. 174°–175°; I.R. max. (KBr) 1690 $cm^{-1}$; $^1H$ NMR ($CDCl_3$) δ 3.84 (1H, d, J=17 liz, C-2/equat. H), 6.24, 6.36 (2H, s, aromatic), 6.86 (1 11, m, C-6H), 9.48 (1H, s, C-7H). Anal. ($C_{25}H_{36}O_3$) C, H. The methyl ether (5c) melts at 109°–110°; $[\alpha]^D+302$ (c, 8.2 mg/ml, $CHCl_3$); I.R. max (neat) 1680 $cm_{-1}$; $^1H$ NMR ($CDCl_3$) δ 3.76 (1H, d, J=18 Hz, C-2 equat. H), 3.80 (3H, s, OCH3), 6.38, (I H, d, J=1.5, arom.), 6.42 (1H, d, J=1.5, arom.), 6.82 (1H, m, C-6 H) , 9.50 (1H, s, C-7H) ; MS m/z 398 ($M^+$). Anal. ($C_{26}H_{38}O_3$) C, H.

5. Synthesis of HU-211, monoacetate (4c)

Potassium (1 g) was added to 2-methyl-2-butanol (16 ml) under a nitrogen atmosphere. The mixture was warmed, at 80°, until all the metal had reacted. The excess alcohol was removed by vacuum distillation and the dry residue was dissolved in dry benzene (45-ml). Two ml of this solution were added to HU-211- (30 mg, 0.78 mmoles) dissolved in dry benzene (30 ml). The solution was stirred, under a nitrogen atmosphere, for 2 hrs., then it was washed with a dilute HCl solution (1N), followed by a sodium bicarbonate solution (1N) and then with water. The organic layer was dried over $MgSO_4$, and evaporated. The oil obtained was chromatographed on silica gel (15 gr.) Elution with ether-:petroleum ether (1:10) gave the diacetate of HU-211 (99 mg) followed by traces of the monoacetate (on the allylic alcohol moiety), eluted with ether:petroleum ether (2:10), followed by the monoacetate (4c), 150 mg, identified by the I.R. peak at 1760 $cm^{-1}$; $^1$H NMR $\delta$ 2.28 (3H, s, $OCOCH_3$), 2.98 (1H, dd, C-2 equat. H), 4.02 (2H, q, C-7H), 5.72 (1H, d, C-6H), 6.52, 6.66 (atom. H).

6. Synthesis of aldehyde (5d)

Dry pyridine (0,645 ml, 8 mmol) was added to methylene chloride:DMF (4:1), followed by chromic oxide (400 mg, 4 mmol). The mixture was stirred at toom temp. for 15 min. The ester (4c) (430 mg, 1 mmol) in the above solvent mixture (2 ml) was added and the reaction mixture was stirred at room temperatue for 16 hrs., then diluted with ethyl acetate (50 ml) and filtered through a sintered glass funnel covered with a 3 cm layer of silica, with a layer (1 cm) of anhydrous magnesium sulphate over it. Ethyl acetate (200 ml) was passed through this double layer; the solvents were evaporated and the residue was chromatographed on silica, using ether:petroleum ether (1:5), yielding the aldehyde (5d) 280 mg (66%) as an oil, identified by the I.R. peaks at 1760 $cm^{-1}$ (phenolic acetate) and 1680 $cm^{-1}$ (unsaturated aldehyde); $^1$H NMR $\delta$ 2.20 (3H, s, $OCOCH_3$), 2.82 (IH, dd, C2 equat. H), 6.42, 6.58 (arom. H), 6.70 (C-6H), 9.40 (aldehyde H). This aldehyde was used without further purification.

7. Synthesis of (3S, 4S) -THC-DMH-7-oic acid, acetate (3c) (HU-245)

Sodium chlorite (488 mg, 4.3 mmol) was added portionwise with vigorous stirring to a mixture of the aldehyde (5d) (4.26 mg, 1 mmole), 2-methyl-2-butene (2.24 ml, 21 mmole), saturated sodium hydrogen phosphate (1.34 ml) and t-butanol (22 ml). The reaction mixture was stirred for 5h. at room temp., extracted with ethyl acetate, dried over magnesium sulphate and the solvent was removed. The acid obtained (390 mg, 88%), m.p. 120°–122° (from pentane) was identical to the material described above.

PHARMACOLOGICAL EXAMPLES

1. Relief of Edema Induced by Arachidonic Acid and PAF

The induction of paw edema in rodents by injection of arachidonic acid has been used as an experimental model for inflammation [Calhoun, W., et al., Agents and Actions, 21, 306 (1987)]. Prior administration of non-steroidal anti-inflammatory drugs (NSAIDs) in many cases leads to a dose related inhibition of the edematous response which may be considered a predictor of clinical efficacy. The cannabinoid acid HU-235, and related compounds were effective in reducing paw edema in this model as seen in Table 1.

A second model, in which edema is induced by platelet activating factor (PAF), was used to evaluate activity. As may be seen from the results summarized in Table II, the acid HU-235 and related compounds were found to be active.

The conditions were based on those reported previously [Calhoun et al., ibid.]. Water was substituted for mercury as the displacement medium and was found to give satisfactory results. PAF (1.0 µq) or arachidonic acid (1.0 mg) dissolved in 50 µl of 5% ethanol in saline, were injected s.c. into the plantar surface of the right hind paw of CD-1 female mice (20–25 g) obtained from Charles River Labs. The mice were under ether anesthesia during this procedure. The volume of the right foot was measured to the level of the lateral malleotis by water displacement before treatment and 15 min after PAF injection or 30 min after archidonate injection. The change in paw volume was calculated for each mouse and the significance for each group was determined by a paired t test analysis.

TABLE I

Inhibition of Arachidonic Acid-Induced Paw Edema[1]

| Dose (mg/kg)[2] | HU-245 (3c) | 7a | 7b | HU-235 (3a) |
|---|---|---|---|---|
| 0.050 | 35.7 (N.S.) | 5.5 (N.S.) | 48.5[3] | 42.1 (N.S.) |
| 0.100 | 50.1[3] | 10.2 (N.S.) | | |
| 0.250 | 48.2[3] | 40.1 (N.S.) | | |
| 0.55 | 42.2 (N.S.) | 47.2[3] | | |

[1] Values shown are percent inhibition of paw edema when compared to vehicle treated controls.
[2] Control mice were given peanut oil (50 µl) orally.
[3] 95% significance by ANOVA. N.S. - nonsignificant.

TABLE II

Inhibition of PAF-Induced Paw Edema[4]

| Treatment | Dose mg/kg[5] | | | | | |
|---|---|---|---|---|---|---|
| | 0.05 | 0.10 | 0.25 | 0.5 | 1.0 | 40.0 |
| HU-235 (3a) | 44.4 N.S. | 38.7[6] | 31.9[6] | 60.1[6] | — | — |
| HU-245 (3c) | | 37.3[6] | 66.9[6] | 72.0[6] | — | — |
| (7b) | | 39.0[6] | 59.0[6] | 68.2[6] | — | — |
| HU-211 (1a) | — | — | 37.5 | 21.9 | — | |
| $\Delta^6$-THC-7-oic acid | — | — | N.S. | N.S. | | 50.2 |

[4] Values shown are percent inhibition of paw edema when compared to vehicle treated controls.
[5] Control mice were given peanut oil (50 µl) orally.
[6] 95% significance by ANOVA. N.S. - nonsignificant.

2. Decreased Adhesion of Leukocytes

Leukocytes are thought to be major contributors to the inflammatory response and their ability in this regard is reflected by their adhesiveness to a variety of substrates [Audette, C. A., et al., ibid.] Sci., 47, 753 (1990)]. The data in Table III show that peritoneal leukocytes from mice orally administered with the present cannabinoids exhibit decreased adhesion.

The details of the leukocytes adhesion assay have been previously reported [Audette et al., ibid.]. In brief, peritoneal cells from female CD-1 mice (20–25 g) were collected at 90 min following oral administration of the drug or vehicle (50 µl peanut oil). Cells from each treatment group (N=3) were pooled and equal numbers aliquoted into six culture dish wells (1.9 $cm^2$ area). After incubation for 18–20 hours, non-adhering cells were removed and the remaining cell monolayer quantitated by DNA measurement.

TABLE III

Effects of Leukocyte Adhesion[7]

| Dose (mg/kg)[7] | HU-211 (1a) | HU-245 (3c) | HU-235 (3a) |
|---|---|---|---|
| Control | 0.88 ± 0.08(100) | 1.26 ± 0.05(100) | 1.26 ± 0.05(100) |
| 0.01 | — | — | 1.34 ± 0.14(106) |
| 0.05 | 1.09 ± 0.08(124)[9] | 1.32 ± 0.04(105)[9] | 1.29 ± 0.05(102)[9] |
| 0.10 | 0.44 ± 0.03(50)[9] | 0.66 ± 0.08(124)[9] | 1.38 ± 0.17(110)[9] |
| 0.20 | — | — | — |
| 0.50 | 0.64 ± 0.06(73)[9] | 0.85 ± 0.08(67)[9] | 1.46 ± 0.05(116)[9] |
| 1.00 | 0.59 ± 0.06(67)[9] | 0.30 ± 0.04(24)[9] | 0.70 ± 0.12(56)[9] |
| THC-7-oic Acid | | | |
| Control | 0.81 ± 0.03- | | |
| 20 | 0.67 ± 0.02(90.6)[9] | | |
| 40 | 0.55 ± 0.22(67.9)[9] | | |

[7]Values are the number of adhering cells × 10⁻⁶ ± S.D. Numbers in parentheses are percent of control. For details see Experimental Section.
[8]Control mice were given 50 µl peanut oil orally. Peritoneal cells were collected 90 min. after oral administration of cannabinoids.
[9]95% significance by ANOVA; otherwise not statistically significant.

3. Antinociception

As with many NSAID type drugs, the present cannabinoids also showed activity in the mouse hot plate test (55° C.) for antinociception.

In the hot plate test for analgesia an aluminum surface was maintained at 55±1° C. by circulating water through passages in the metal. A clear plastic cylinder 18 cm in diameter and 26 cm high was placed on the surface to prevent escape. The end point was taken when the mouse either performed a hind paw lick or jumped off the surface; in no case were the animals kept for more than 30 secs on the plate. Mice were never used more than one time; control values were always measured at 11 a.m. and test values at 2 p.m. The drugs were administered orally 90 min before the hot plate test. The percent change in response time (latency) was calculated by comparing the mean of the control values with the mean of the test values and statistical signficance determined by a paired tetest analysis using software (Statview, 512) from Brainpower, Inc., Calabasas, Calif.

TABLE IV

ANTINOCIOPCEPTIVE EFFECTS[10]

| Dose (mg, kg) | HU-241 (1a) | 3e | HU-245 (c) | HU-235 (3a) |
|---|---|---|---|---|
| 0.025 | — | — | 10.7(5) | 10.3(5) |
| 0.050 | — | — | 66.2(5)[11] | 61.7(5)[11] |
| 0.10 | — | — | 62.2(5)[11] | 49.5(20)[11] |
| 0.25 | 30.0(5)[11] | 10.4(5) | 68.1(10)[11] | 61.5(17)[12] |
| 0.50 | 72.5(5)*** | 49.0(10)[11] | 49.9(5)[11] | 61.5(17)[11] |
| 1.0 | −10.2(5) | 61.4(15)[11] | 12.5 | 51.7(8)[11] |
| 2.0 | — | 37.5(10) | — | 14.7(5) |
| 4.0 | — | 3.1(10) | — | — |

[10]Values are the percent change in latency. See above for details. FIGURES in brackets are the number of mice.
[11]P < 0.05;
[12]**P < 0.005 by a paired t test; otherwise not statistically significant.

4. Cataleptic Effects

The lack of CNS activity for the compounds described herein may be seen from the data shown in Table V. This was measured by the so-called "ring test" [Pertwee, R. G., et al., J. Pharmacol., 46, 753 (1972)] in which the cataleptic effects of cannabinoids can be quantitated. The compounds produced little or no response when compared with the parent drug.

The cataleptic response was measured using the ring test. Mice were placed on a horizontal wire ring 5.5 cm in diameter, which was attached to a 16 cm vertical rod. The hind paws and fore paws were placed at opposite sides of the ring. It is important that the ambient temperature is maintained at 30° C. and that the environment be free of auditory stimuli and bright lights. The criteria for immobility are detailed by Pertwee. The response is calculated as the fraction of time the mouse is immobile over a 5 min. test period. Measurements were always done between 2 and 4 p.m. and the animals were used only once.

TABLE V

CATALEPTIC EFFECTS IN THE MOUSE[13]

| Treatment | Dose (mg/kg) | Response + SD |
|---|---|---|
| Vehicle[14] | — | 7.7 ± 4.4 |
| HU-245 (3c) | 0.5 | 6.8 ± 2.4 |
| HU-245 (3c) | 1.0 | 12.0 ± 6.0 |
| HU-235 (3a) | 0.25 | 12.3 ± 10.3 |
| HU-235 (3a) | 0.5 | 13.8 ± 7.9 |
| KU-235 (3a) | 1.0 | 10.4 ± 10.6 |
| HU-235 (3a) | 4.0 | 8.7 ± 5.6 |
| Δ¹-THC | 40 | 48.9 ± 16[15] |

[13]The values are expressed as the means of the fraction of time the mice remained immobile ± SD. See above for other details.
[14]Peanut oil (50 µl) given orally.
[15]5% significance by ANOVA; otherwise not statistically significant.

The present compounds are active in several tests generally used to indicate neuroprotection. For example, HU-245 which was investigated most thoroughly, is a blocker of N-methyl-D-aspartate (NMDA) and picrotoxin induced lethality in mice, as seen previously for HU-211 (compound la) (Israel Patent Application No. 92238). It also protects against strychnine induced lethality in rats. Compounds HU-211 (1a), HU-235 (3a) and HU-245 (3c) have also been shown to protect against forebrain ischemia (unilateral occlusion) in mongolian gerbils.

Balb/c male mice were administered with the drug 90 min before treatment with NMDA (125 mq/kg) or 120 min before picrotoxin (8 mg/kg) in emulsion, s.c. The survival rate shown in Table VI indicates number of survivors out of total number of animals used.

TABLE VI

| Toxin | Drug | Survival rate |
|---|---|---|
| Picrotoxin | — | 0/17 |
| Picrotoxin | HU-245 (10 mg/kg) | 5/8 |
| Picrotoxin | HU-211 (10 mg/kq) | 6/10 |
| Picrotoxin | HU-235 (10 mg/kg) | 8/12 |
| NMDA | — | 0/20 |
| NMDA | HU-245 (2.5 mg/kg) | 6/12 |
| NMDA | HU-245 (10 mg/kg) | 8/10 |
| NMDA | HU-235 (10 mg/kg) | 7/10 |
| NMDA | HU-211 (10 mg/kg) | 11/16 |

6. Anti-Glaucoma Activity

Reduction of intraocular pressure in rabbits was determined by the addition of a 50 µl drop of a 1% emulsion of the cannabinoid into the rabbit eye. This test is a measure of anti-glaucoma activity. Significant reduction was established for compounds HU235 and Hu-245.

7. NMDA-blocking Response in Oocytes

The oocyte is the most widely used system for studying the molecular, biophysical. and pharmacological properties of expressed voltage- or transmitter-operated ion channels. This giant cell offers several advantages for this type of studies. It can be readily used for two-electrode voltage clamp studies, translates injected mRNA from different sources and functionally expresses the translated proteins, and it is also readily amenable for intracellular microinjections. Importantly, the recordings of transmitter or voltage-induced currents in a single oocyte are extremely stable and can be done, without rundown, for 2–3 hours; this allows the performance of a full dose-response relation in single oocytes.

Neuronal receptors for excitatory amino acid (EAA) are becoming increasingly important for the understanding of normal and pathological brain function. Quantitative pharmacological studies of EAA receptor/ion channel. complex are difficult to study in neurons. Therefore, Xenopus oocyte injected with brain MRNA is now the preparation of choice.

The response to N-methyl-D-aspartate (NMDA) in oocytes injected with rat brain mRNA was characterized and the effects of HU-245 were studied.

Female Xenopus were anesthetized by immersion in water containing 0.15% tricaine methanesulfonate and a small incision was made in the lower abdomen. Ovary fragments were removed into ND-96. The frog was allowed to heal for at least three months before using again.

The oocytes were defolliculated by the collagenase treatment in order to remove the follicle cell layer. Defolliculated oocytes were injected with total rat brain RNA and incubated for 2–4 days at 220° C. in sterile NDE-96 solution. ND-96 solution contains (in mm): NaCl 96, KCl 2, CaCl2 1.8, Hepes 5 (pH=7.4–7.6). NDE-96 contains in addition, 2.5 mM sodium pyruvate, 100 unit/ml penicillin, 100 µg/ml streptomycin.

A single oocyte was placed in a 1 ml bath constantly superfused with ND-96 solution at room temperature. The cell was impaled with two microelectrodes and held at membrane potential of –60 mV using voltage clamp circuit.

RNA was extracted from brain of 14-day old rat brain. Each oocyte was injected with 50 nl total RNA (48 mg/ml in water, stored at –80° C. in 3–10 nl aliquots).

All chemicals were from Sigma.

Oocytes injected with rat brain RNA became responsive to all EAA (NMDA, kainate, glutamate) and to other transmitters (5HT, GABA, etc.). The conductance activated by NMDA was examined more closely. In most oocytes NMDA alone did not evoke any detectable currents, and the addition of glycine was necessary in order to evoke a response. Therefore, to observe an NMDA response, the-combination: $10^{-4}$M NMDA $5\times10^{-6}$M glycine was used in all the experiments.

Several NMDA receptor blockers were tested. These compounds have very low solubility and have to be dissolved in 100% dimethyl sulfoxide (DMSO) and diluted for use in ND 96 that contained 1% DMSO. Therefore, the effect of 1% DMSO on the response to $10^{-4}$M NMDA and $5\times10^{-6}$M glycine was examined. DMSO had no effect on NMDA response in three different cells.

The new derivative HU-245 was tested on the NMDA response at a concentration of $10^{-6}$M. A complete blocking effect could not be achieved since the compound is only soluble at a concentration of up to $10^{-7}$M. Compound HU-245 had a strong inhibitory effect on the response to NMDA-55% of control at $10^{-6}$M. Another advantage of HU-245 seems to be its solubility, which is higher than that of prior art compounds. The effect of HU-245 was reversible upon return to ND 96 solution.

While the present invention has been illustrated hereinabove with various specific examples, those skilled in the art will recognize that many other specific embodiments of this invention can be made. All such other specific embodiments likewise constitute aspects of the present invention, the protected scope of which is to be determined solely by the appended claims.

We claim:

1. A compound of the general formula

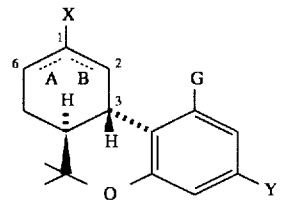

having the (3S,4S) configuration and being essentially free of the (3R,4R) enantiomer, in which A . . . B indicates an optional 1(2) or 6(1) double bond, X is —C(O)OR" wherein R" is hydrogen or $C_1$–$C_5$ alkyl optionally containing a terminal —OR'" or —OC(O)R'" moiety wherein R'" is hydrogen or $C_1$–$C_5$ alkyl, —R'C(O)OR" wherein R' is $C_1$–$C_5$ alkyl and R" is hydrogen or $C_1$–$C_5$ alkyl optionally containing a terminal —OR'" or —OC(O)R'" moiety wherein R'" is hydrogen or $C_1$–$C_5$ alkyl, —C(O)N(R")$_2$ wherein each R", which may be the same or different, is hydrogen or $C_1$–$C_5$ alkyl optionally containing a terminal —OR'" or —OC(O)R'" moiety wherein R'" is hydrogen or $C_1$–$C_5$ alkyl, or —R'C(O)N(R")$_2$ wherein R' is $C_1$–$C_5$ alkyl and each R", which may be the same or different, is hydrogen or $C_1$–$C_5$ alkyl optionally containing a terminal —OR'" or —OC(O)R'" moiety wherein R'" is hydrogen or $C_1$–$C_5$ alkyl, G is —OR" wherein R" is hydrogen or $C_1$–$C_5$ alkyl optionally containing a terminal —OR'" or —OC(O)R'" moiety wherein R'" is hydrogen or $C_1$–$C_5$ alkyl or —OC(O)R" wherein R" is hydrogen or $C_1$–$C_5$ alkyl optionally containing a terminal —OR'" or —OC(O)R'" moiety wherein R'" is hydrogen or $C_1$–$C_5$ alkyl, and Y is $C_1$–$C_{12}$ straight chain or branched alkyl, —OR"" wherein R"" is a straight-chained or branched $C_2$–$C_9$ alkyl which may be substituted at the terminal carbon atom by a phenyl group, or —(CH$_2$)$_n$OR'" wherein n is an integer of from 1 to 7 and R'" is hydrogen or $C_1$–$C_5$ alkyl.

2. A compound as in claim 1 wherein X is —C(O)OR" or —R'C(O)OR".

3. A compound as in claim 1 wherein X is —C(O)N(R")$_2$ or —R'C(O)N(R")$_2$.

4. A compound as in claim 1 wherein G is —OR".

5. A compound as in claim 1 wherein Y is C$_1$–C$_{12}$ straight chain or branched alkyl.

6. A compound as in claim 1 of the formula:

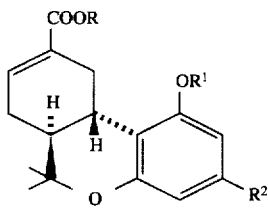

wherein R is a hydrogen atom or a C$_1$–C$_5$ alkyl group, R$^1$ is a hydrogen atom or a C$_1$–C$_5$ acyl group, and R$^2$ is selected from the group consisting of: (a) a straight-chained or branched C$_1$–C$_{12}$ alkyl; (b) a group —O—R$_4$, wherein R$_4$ is a straight-chained or branched C$_2$–C$_9$ alkyl which may be substituted at the terminal carbon atom by a phenyl group; and (c) a group —(CH$_2$)$_n$-O-alkyl, where n is an integer of from 1 to 7 and the alkyl group contains from 1 to 5 carbon atoms.

7. A compound according to claim 6 wherein R is hydrogen, R$^1$ is hydrogen or methyl, and R$^2$ is 1,1-dimethylheptyl.

8. A compound according to claim 6 having the formula

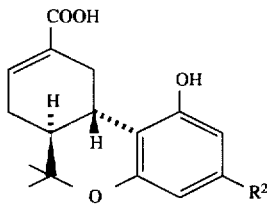

9. A compound according to claim 1 wherein A . . . B indicates a 6(1) double bond, X is carboxy, G is acetoxy, and R is 1,1-dimethylheptyl.

10. A compound according to claim 1 wherein A . . . B indicates a 6(1) double bond, X is N,N-diethylcarboxamide, G is acetoxy, and R is 1,1-dimethylheptyl.

11. A compound according to claim 1 wherein A . . . B indicates a 6(1) double bond, X is N-β-hydroxyethylcarboxamide, G is acetoxy, and R is 1,1-dimethylheptyl.

12. A pharmaceutical composition having analgesic, antiemetic, sedative, anti-inflammatory, anti-glaucoma, or neuroprotective activities which contains as an active ingredient a therapeutically effective quantity of a compound of claim 1.

13. A pharmaceutical composition having analgesic, antiemetic, sedative, anti-inflammatory, anti-glaucoma, or neuroprotective activities which contains as an active ingredient a therapeutically effective quantity of a compound of claim 9.

14. A pharmaceutical composition having analgesic, antiemetic, sedative, anti-inflammatory, anti-glaucoma, or neuroprotective activities which contains as an active ingredient a therapeutically effective quantity of a compound of claim 10.

15. A pharmaceutical composition having analgesic, antiemetic, sedative, anti-inflammatory, anti-glaucoma, or neuroprotective activities which contains as an active ingredient a therapeutically effective quantity of a compound of claim 11.

16. A pharmaceutical composition according to one of claims 12–15 containing a pharmaceutically acceptable diluent or carrier.

17. A pharmaceutical composition according to claim 16 wherein the diluent is an aqueous cosolvent solution comprising a pharmaceutically acceptable cosolvent, a micellar solution prepared with natural or synthetic ionic or nonionic surfactants, or a combination of such cosolvent and micellar solutions.

18. A pharmaceutical composition according to claim 16 which comprises a carrier consisting essentially of a solution of ethanol, a surfactant, and water.

19. A pharmaceutical composition according to claim 16 which comprises a carrier consisting essentially of an emulsion comprising triglycerides, lecithin, glycerol, an emulsifier, an antioxidant, and water.

20. A pharmaceutical composition according to one of claims 12–15 in unit dosage form.

21. A pharmaceutical composition according to claim 20 wherein the daily dosage of said compound is from 0.005 to about 50 mg/kg.

22. A pharmaceutical composition according to claim 21 wherein said daily dosage is from about 1 to about 20 mg/kg.

23. A compound as claimed in claim 1 wherein A . . . B is not present; X is C(O)OR"; G is OC(O)R; and Y is a branched C$_1$ to C$_{12}$ alkyl group.

24. A compound as claimed in claim 1 wherein A . . . B is not present; X is C(O)OH; G is OC(O)CH$_3$; and Y is 1,1-dimethylheptyl.

* * * * *